United States Patent
Pang et al.

(10) Patent No.: US 8,357,281 B2
(45) Date of Patent: Jan. 22, 2013

(54) MULTI-WAVELENGTH FLUORESCENCE DETECTION SYSTEM FOR MULTIPLEXED CAPILLARY ELECTROPHORESIS

(75) Inventors: Ho-Ming Pang, Ames, IA (US); Wei Wei, Ames, IA (US)

(73) Assignee: Advanced Analytical Technologies, Inc., Ames, IA (US)

( * ) Notice: Subject to any disclaimer, the term of this patent is extended or adjusted under 35 U.S.C. 154(b) by 232 days.

(21) Appl. No.: 12/883,475

(22) Filed: Sep. 16, 2010

(65) Prior Publication Data

US 2011/0068007 A1    Mar. 24, 2011

Related U.S. Application Data

(60) Provisional application No. 61/244,275, filed on Sep. 21, 2009.

(51) Int. Cl.
  *G01N 27/00* (2006.01)
(52) U.S. Cl. ........................... 204/603; 204/601
(58) Field of Classification Search ................. 204/601, 204/603
See application file for complete search history.

(56) References Cited

U.S. PATENT DOCUMENTS

| | | | |
|---|---|---|---|
| 5,468,364 A | 11/1995 | Fujii | |
| 5,582,705 A | 12/1996 | Yeung et al. | |
| 5,741,411 A | 4/1998 | Yeung et al. | |
| 6,048,444 A | 4/2000 | Takahashi et al. | |
| 6,100,535 A | 8/2000 | Mathies et al. | |
| 6,118,127 A | 9/2000 | Liu et al. | |
| 6,270,644 B1 | 8/2001 | Mathies et al. | |
| 6,461,492 B1 * | 10/2002 | Hayashizaki et al. | 204/603 |
| 6,554,986 B1 | 4/2003 | Mathies et al. | |
| 6,833,062 B2 | 12/2004 | Kennedy et al. | |
| 6,833,919 B2 | 12/2004 | Kenseth et al. | |
| 6,969,452 B2 | 11/2005 | He et al. | |
| 7,083,711 B2 | 8/2006 | Wei | |
| 7,118,659 B2 | 10/2006 | Kurt et al. | |
| 7,497,937 B2 | 3/2009 | Yeung et al. | |
| 7,534,335 B2 | 5/2009 | Kennedy et al. | |
| 2004/0184960 A1 * | 9/2004 | Tanaami | 422/82.05 |

* cited by examiner

*Primary Examiner* — Luan Van
*Assistant Examiner* — Steven Rosenwald
(74) *Attorney, Agent, or Firm* — McKee, Voorhees & Sease, P.L.C.

(57) ABSTRACT

Using multiple dichroics mirrors to split and redirect different wavelength regions of light in a multi-wavelength fluorescence detection system.

4 Claims, 6 Drawing Sheets

MULTI-WAVELENGTH FLUORESCENCE DETECTION SYSTEM FOR MULTIPLEXED CAPILLARY ELECTROPHORESIS

CROSS-REFERENCE TO RELATED APPLICATIONS

This application claims priority under 35 U.S.C. §119 of a provisional application Ser. No. 61/244,275 filed Sep. 21, 2009, and which application is hereby incorporated by reference in its entirety.

FIELD OF THE INVENTION

This invention relates to a multiplexed capillary electrophoresis (CE) multi-wavelength fluorescence detection systems and methods that may be used for the separation and detection of substances possessing fluorescent properties, e.g., fluorescently labeled dsDNA, amino acids, carbohydrates, fatty acids, proteins, etc.

BACKGROUND OF THE INVENTION

Capillary electrophoresis (CE) systems use electric fields to separate molecules within narrow-bored capillaries while the capillaries are filled with conductive buffers or gel matrix. Samples are injected into the capillary tubing for separation under the high electric field or hydrodynamic flow. Sample molecules are detected by different means while passed through the detection window. UV absorption detection is the most common detection means since almost all analytes have UV absorption property. However, because of the use of narrow-bored capillaries ($\leq 100$ μm I.D.) for absorption measurement and the measurement of a small light intensity change from a high background light source, sensitivity is limited at $10^{-5}$ M levels. Laser induced fluorescence (LIF) detection can also be used in capillary electrophoresis for samples that naturally fluoresce or are chemically modified to contain fluorophores. LIF provides much higher sensitivity than the UV absorption detection due to the ultra low background. However, the use of laser as excitation light source in fluorescent detection is expensive and difficult to maintain. Alternatively, Xenon lamp or light emitted diode (LED) have been used for fluorescent excitation light source.

In order to improve the sample throughput, multiple capillaries are used to analyze multiple samples simultaneously, these multiplexed capillary array electrophoresis systems are used in many commercial DNA sequencers. Most of them use a laser as the light source, including confocal scanning laser induced fluorescence (e.g. U.S. Pat. No. 6,270,644), sheath flow detectors (e.g. U.S. Pat. Nos. 5,468,364 and 6,048,444), side-entry optical excitation geometry (e.g., U.S. Pat. Nos. 5,582,705 and 5,741,411), and fiber optics for excitation and emission collection (U.S. Pat. No. 6,870,165).

There is a need for multiple wavelength measurement during fluorescent detection in CE. For example, DNA sequencing determination in the commercial DNA sequencers requires the measurement of four different wavelength regions to discriminate four different nucleotide bases for sequence determination since each type of nucleotide is labeled with a different fluorescent tag. The dominant signal from different wavelength regions determines the nucleotide base. In some cases, a filter wheel has been used to measure different wavelength regions sequentially by rotating the filter wheel to the desired filters. This method is not efficient since only one wavelength region can be measure at any given time. U.S. Pat. Nos. 6,461,492 and 6,554,986 uses beam splitters to divide the light emission into multiple beams with multiple detectors for multi-wavelength detection. This method measures only one capillary signal at a time and requires a scan of each detection window sequentially for multiplexed capillary array electrophoresis operation. In addition, this method requires the use of multiple detectors for measurement which increases the cost and maintenance substantially. U.S. Pat. No. 6,048,444 reveals a method that used a single detector to measure four different wavelength regions simultaneously. The fluorescent signal is split by an image splitter prism and projected into a two-dimensional detector. Wavelength is selected by using four different filters. However, since the fluorescent emission is split to four regions before filtering, it suffers the low light detection efficiency. U.S. Pat. No. 5,998,796 discloses a method of using a transmission grating for multi-wavelength analysis for multiplexed capillary array electrophoresis. U.S. Pat. No. 5,741,411 revealed a method using a tilted filter to split the fluorescent signal into two for two wavelength fluorescent measurements while using a single two-dimensional detector. However, this method was limited to two wavelength regions measurement.

As can be seen from the state of the art, it would be desirable to develop a low-cost, less complex design resulting in high light detection efficiency, high throughput in multiple-capillaries, and multi-wavelength detection in multiplexed capillary array electrophoresis systems for biological separation to overcome the limitations in the prior art.

SUMMARY OF THE INVENTION

A high sensitivity and high throughput capillary electrophoresis multi-wavelength fluorescence detection system using multiple dichroic mirrors to split and redirect different wavelength regions of the fluorescent images of multiple capillary detection windows on the light collection and detection system. The present system provides maximum collection efficiency to divide the fluorescent signal to multiple regions for later detection. The system allows the use of a single two dimensional detector to monitor a different wavelength region for each capillary simultaneously in a multiplexed capillary electrophoresis system.

DETAILED DESCRIPTION OF THE INVENTION

Figure 1:
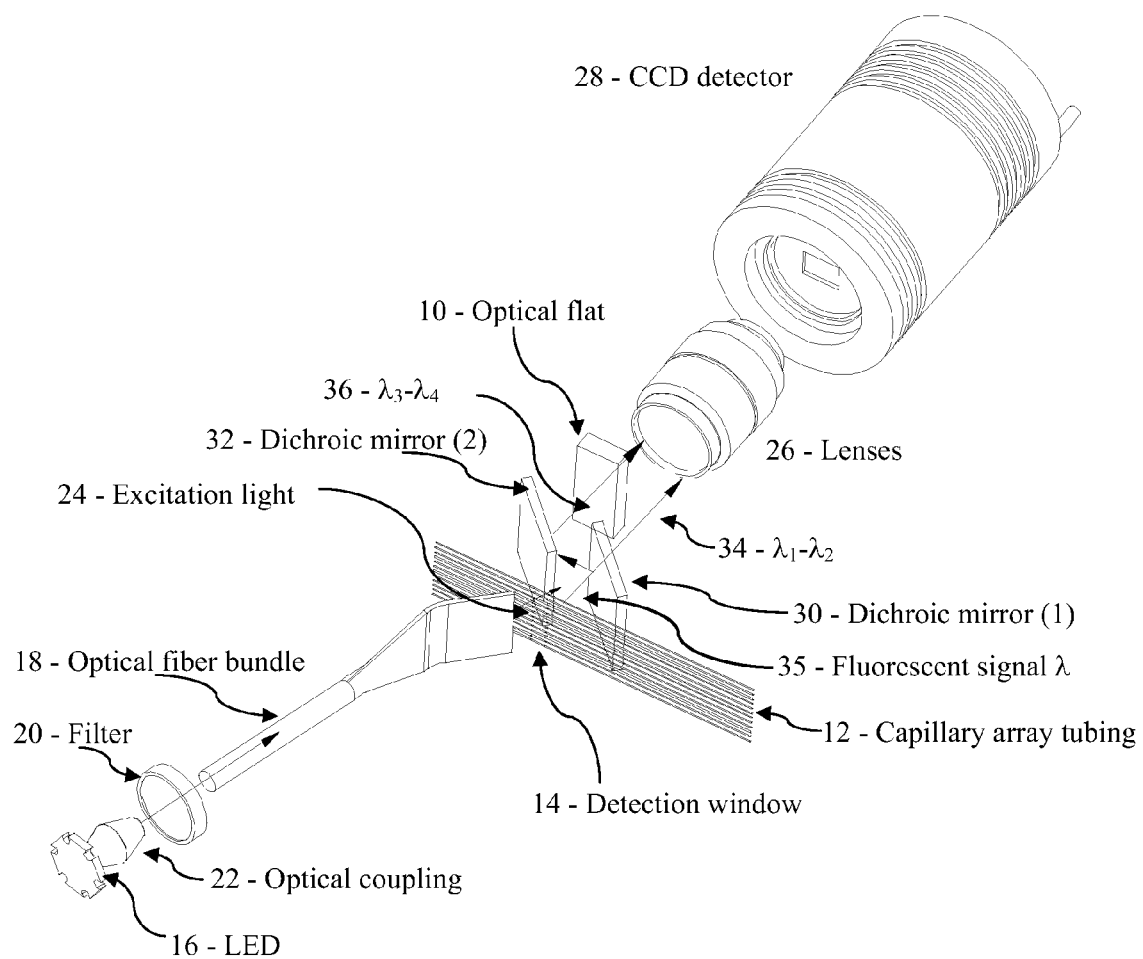
FIG. 1 is a perspective schematic view of a two-wavelength fluorescence detection system for multiplexed capillary electrophoresis in accordance with the present invention.

A specific embodiment of the invention is described in connection with FIG. 1. It is, however, to be understood FIG. 1 is exemplary only and that other physical embodiments of the system may be employed without departing from the scope and spirit of the invention.

Figure 2:
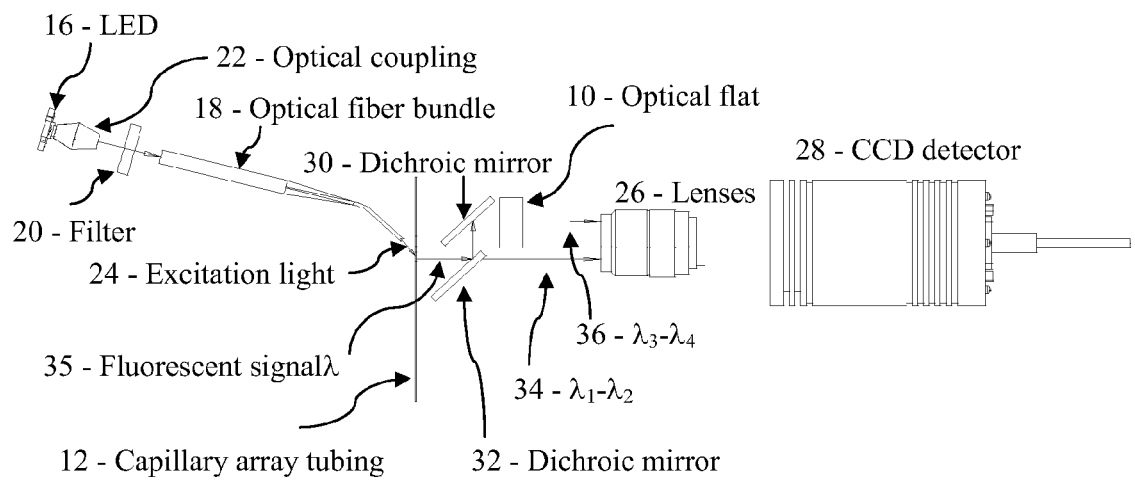
FIG. 2 is a top view of the FIG. 1.

The invention includes a fluorescent detection system for multiplexed capillary electrophoresis. The detection system includes a sample vessel (e.g., a capillary) in which a sample is placed. Multiple capillaries 12 are used here to increase the sample analysis throughput. At the detection location 14, all capillaries are packed in parallel to allow simultaneously excitation and fluorescent detection. The light source could be a light emitting diode, gas discharge lamp, or laser. An optical fiber bundle 18 is used to reshape the light source output from round shape to a line shape to illuminate the detection windows of the sample vessels. In the preferred embodiments, a high power LED 16 is used as preferred light source. A filter 20 is positioned in between the light source and the optical fiber bundle 18 to remove the undesired wavelength. An optical coupler 22 is positioned in between the LED 16 and the optical fiber bundle 18 to improve the light coupling efficiency between the LED 16 and the optical fiber bundle 18. The output of the optical fiber bundle 18 is positioned at an angle from 30 to 70° against the capillary windows 14 to illuminate all detection windows 14 at once. A detection window 14 on the capillary is created by removing a section (~3 mm in length) of the protective polyimide coating. The output light 24 from the optical fiber bundle 18 illuminates the center of the bared capillary windows 14 simultaneously. The lens 26 collects the scattering and fluorescent light from the capillary window and projects the capillary detection window images onto a two dimensional detector such as a CCD camera 28. Dichroic mirror (1) 30 and dichroic mirror (2) 32 are positioned in between the capillary windows 14 and the light collection lens 26 as shown in FIG. 1. FIG. 2 shows the top view of FIG. 1. The fluorescent emission signal of the sample is initially divided by dichroic mirror (1) 30. Wavelength $\lambda_1$ to $\lambda_2$ (34) passes dichroic mirror (1), 30 and is collected by the lens 26 and detected by a two dimensional CCD detector 28. The remaining wavelength $\lambda_3$ to $\lambda_4$ 36 is reflected by dichroic mirror (1) 30, and is redirected by dichroic mirror (2), 32 into the lens 26 and detected by the CCD camera 28. The second dichroic mirror (2) 32 not only redirects the split florescent image $\lambda_3$ to $\lambda_4$ (36) to the camera lens, it also acts as an additional filter to select the $\lambda_3$ to $\lambda_4$ (36) wavelength since dichroic mirror (1) 30 is not 100% efficient to pass the $\lambda_1$ to $\lambda_2$ (34). A small amount of $\lambda_1$ to $\lambda_2$ (34) and the fluorescent excitation wavelength 35 will also be redirected by dichroic mirror (1), 30. The use of second dichroic mirror (2) 32 instead of a total reflected mirror will filter the unwanted wavelength before detection. As an alternative, one could use a simple mirror to reflect the wavelength $\lambda_3$ to $\lambda_4$ (36) but additional filter(s) will be required to filter the unwanted wavelength. In this arrangement, the image of the capillary window is split into two identical images in which one contains wavelength information from $\lambda_1$ to $\lambda_2$ (34) while other image contains wavelength information from $\lambda_3$ to $\lambda_4$ (36). The second image is shifted to a define position controlled by the spacing between the dichroic mirrors. By carefully positioning the space in between the dichroic mirrors, one could use a single two dimensional detector to capture both images simultaneously. Software could then be used to extract the information for each capillary window to display time lapse result as electropherogram for each wavelength region. in addition, in order to compensate the different light paths for $\lambda_1$ to $\lambda_2$ (34) and $\lambda_3$ to $\lambda_4$ (36), an optical flat 10 or additional filter could be positioned in between the dichroic mirror (2) 32 and the camera lens 26 to increase $\lambda_3$ to $\lambda_4$ (36) light path so that both wavelength images could be focused on the CCD detector (28).

Figure 3:
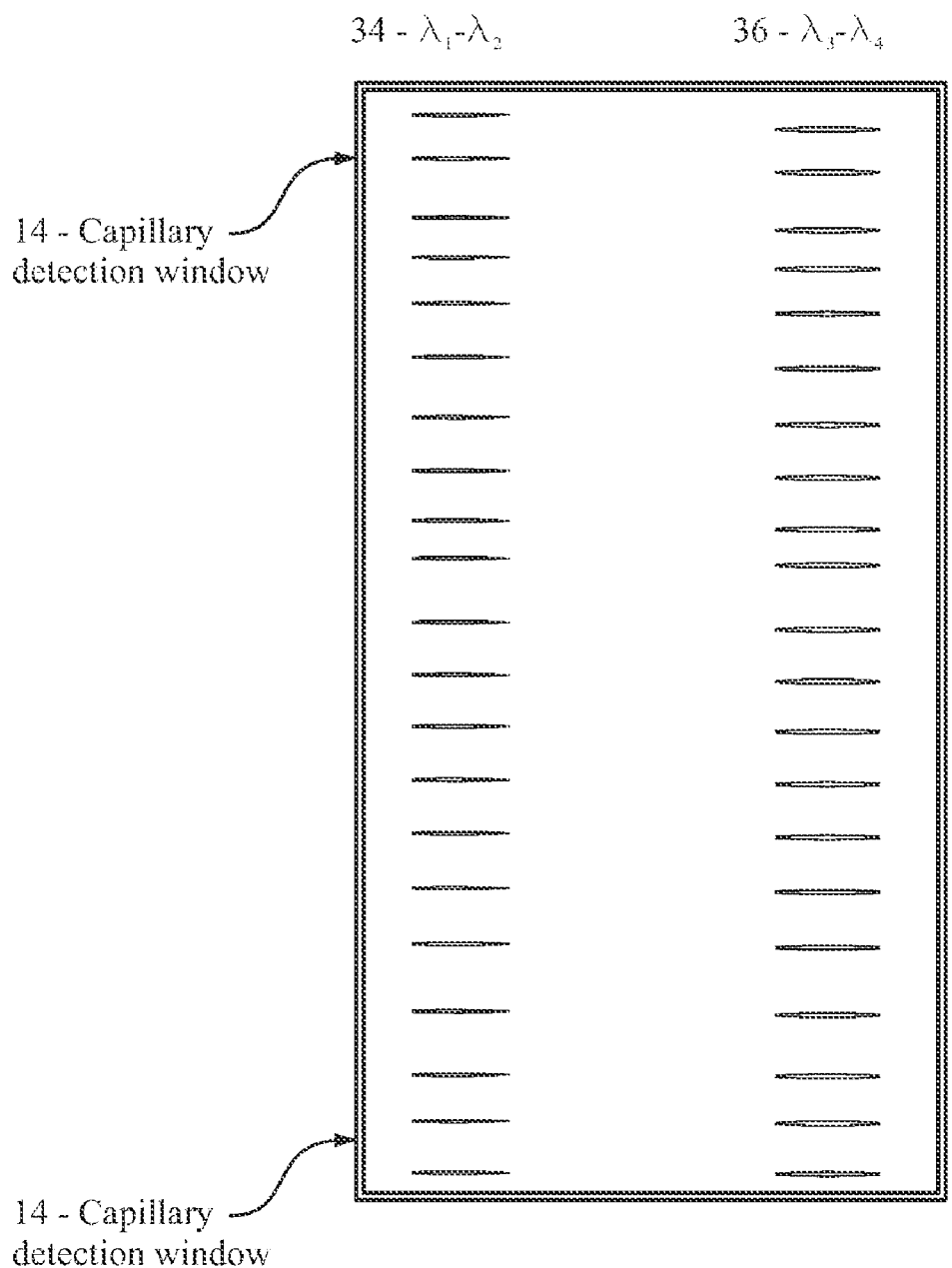
FIG. 3 is the 2D image readout from the two-dimensional detector with the present invention.

FIG. 3 shows the result of the CCD camera output image with the present invention. Twenty-one capillaries were used here for the purpose of illustration. Each capillary detection window was illuminated by the light output from the optical fiber bundle. ~2 mm of detection window was illuminated for fluorescent measurement. All capillaries windows are monitored simultaneously. The lens projected the capillary illuminated window image onto the CCD camera. Due to imperfect removal of the protective coating or imperfect surface on the capillary detection window, one could observe a different intensity distribution within the capillary detection window. The images of the capillaries detection windows were split into two by the present invention. One image retains the pass-through wavelength information from $\lambda_1$ to $\lambda_2$ (34) while the second image contains the reflected wavelength information from $\lambda_3$ to $\lambda_4$ (36). The present apparatus allows monitoring two different wavelength regions simultaneously for multiple capillary array electrophoresis with a single detector. In order to form an electropherogram, one could monitor the intensity change on the capillary detection window over time. For example, one could simply add all the individual pixilated intensities together; i.e. all pixels in the detection window (small boxes) in FIG. 3(*b*) to represent the intensity signal of the particular capillary.

Figure 4:
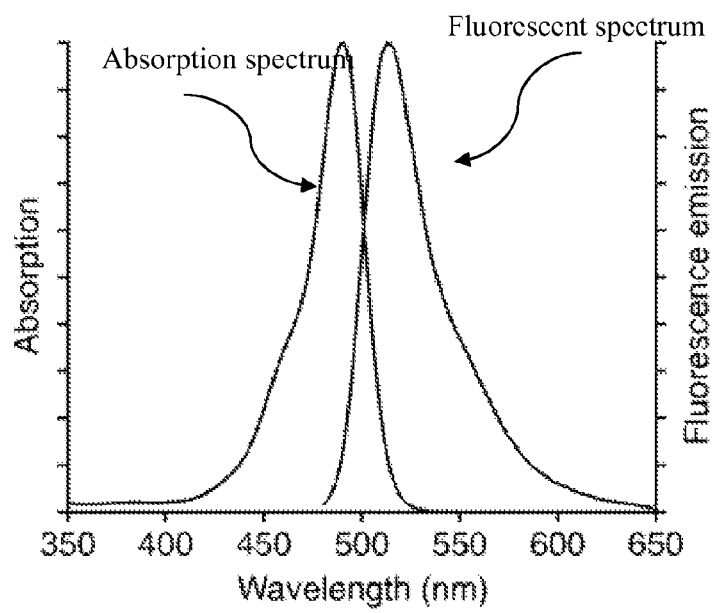
FIG. 4 is electropherograms from each wavelength using the system of FIG. 1.
Figure 5:
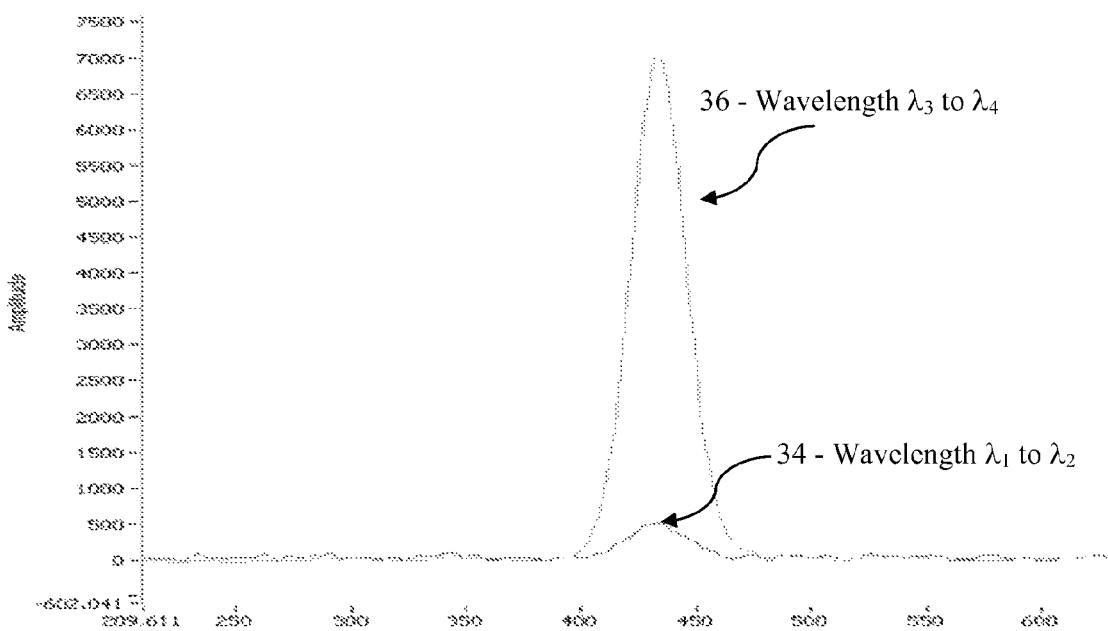
FIG. 5 is the absorption and fluorescent spectra of fluorescein.

For example, when fluorescein is used as a sample and injected and analyzed by the present invention, the fluorescein fluorescent light at the detection window will be split into two separate beams. If one uses a dichroic beam splitter with reflection band from 490 nm to 528 nm ($\lambda_3$ to $\lambda_4$) and transmission band from 547 nm to 690 nm ($\lambda_1$ to $\lambda_2$), the pass-through image will contain the wavelength information from 547 nm to 690 nm ($\lambda_1$ to $\lambda_2$) while the reflected image will contain the wavelength information from 490 nm to 528 nm ($\lambda_3$ to $\lambda_4$). FIG. 4 shows the excitation and fluorescent spectra of fluorescein. From FIG. 4, one could easily determine that the signal from the green region of the wavelength ($\lambda_3$ to $\lambda_4$) will be much stronger than the red region of the wavelength ($\lambda_1$ to $\lambda_2$). One could sum all related pixels together from the CCD image to represent the fluorescent intensity for each capillary. A time-lapsed trace (electropherogram) could be generated by monitoring the intensity change of each fluorescent wavelength region over a period of time. FIG. 5 shows the electropherograms of one of the capillary. Each trace of electropherogram represented one wavelength region. As the result of the different wavelength intensity distribution, the green region electropherogram ($\lambda_3$ to $\lambda_4$) will have significantly stronger signal than the red wavelength region ($\lambda_1$ to $\lambda_2$) as shown depicted by the fluorescent spectrum.

Figure 6:
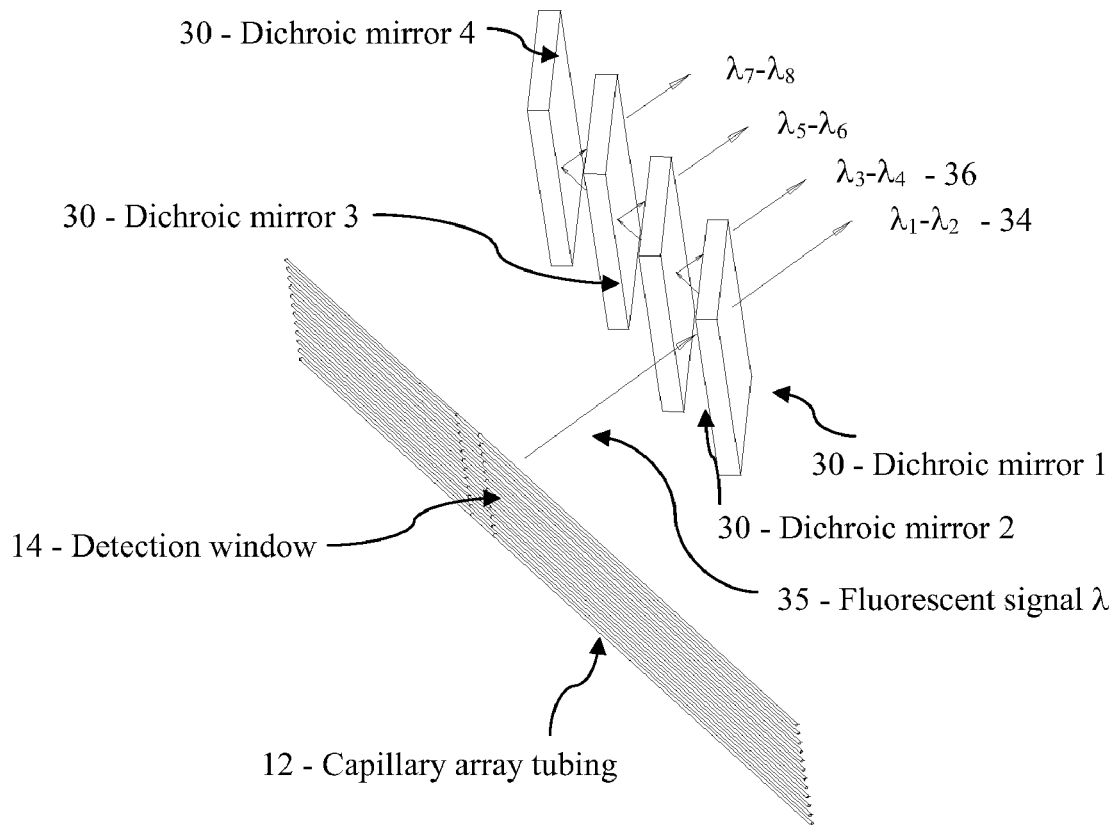
FIG. 6 is a perspective schematic view of a multi-wavelength fluorescence detection system for multiplexed capillary electrophoresis in accordance with present invention.
Figure 7:
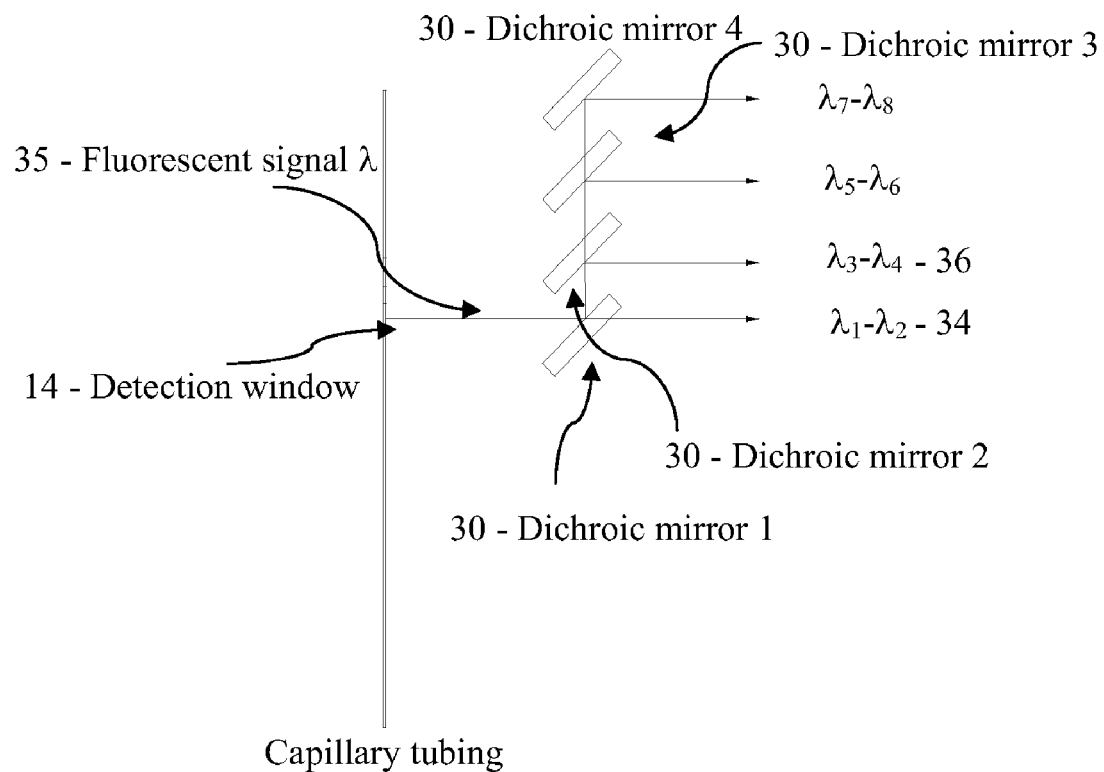
FIG. 7 is a top view of the FIG. 6.

This beam splitting scheme not only can divide the wavelength into two regions, one could use the same principle to divide the wavelength into multiple regions. For example, FIG. 6 shows the prospective view of multi-wavelength setup of the present invention while FIG. 7 shows the top view of the setup. Both figures illustrate one could split the fluorescent wavelength into four different regions, i.e. for each detection window of a multiplexed capillary array, the CCD camera will observe four images and each image represents different wavelength regions. Four dichroic mirrors are used to here to split and redirect the fluorescent signals from the capillary array detection windows. Four different wavelength region images ($\lambda_1$ to $\lambda_2$, $\lambda_3$ to $\lambda_4$, $\lambda_5$ to $\lambda_6$, and $\lambda_7$ to $\lambda_8$) could be observed by the camera lens and the two dimensional CCD detectors simultaneously. Different wavelength region electropherograms could then be formed by monitoring desired region intensity change on the CCD detector overtime.

From the above disclosure it can be seen that the invention accomplishes at least its stated objectives of low cost, less complex design and at the same time high light detection efficiency.

What is claimed is:

1. In a multi-wavelength fluorescence detection system having, a plurality of side-by-side capillaries disposed in a plane, a light source positioned to direct a beam of light through each capillary to induce a fluorescent emission from any samples in the capillaries, a light collection lens to collect fluorescent emissions from said samples, and a detector positioned to receive said emissions from said collector lens, the improvement comprising: using multiple dichroic mirrors to split and redirect different wavelength regions of said emissions to said detector to monitor a different wavelength region for each capillary simultaneously, placing an optical flat between the multiple dichroic mirrors and the lens to increase the light path of one of the redirected wavelength regions.

2. The system of claim 1 which uses at least two dichroic mirrors positioned between the capillary array and the collector lens.

3. The system of claim 2 wherein the spacing between the dichroic mirrors is carefully controlled to allow use of a single two dimensional detector.

4. The system of claim 2 wherein an optical filter is placed between the second of the at least two dichroic mirrors and the lens so both wavelength regions can be focused on the detector.

* * * * *